United States Patent
Siegler et al.

(10) Patent No.: US 10,433,970 B2
(45) Date of Patent: *Oct. 8, 2019

(54) PROSTHETIC ANKLE

(71) Applicant: Drexel University, Philadelphia, PA (US)

(72) Inventors: Sorin Siegler, Merion Station, PA (US); Jason R. Toy, Medford, NJ (US)

(73) Assignee: DREXEL UNIVERSITY, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/919,983

(22) Filed: Mar. 13, 2018

(65) Prior Publication Data

US 2018/0256349 A1    Sep. 13, 2018

Related U.S. Application Data

(63) Continuation of application No. 14/772,346, filed as application No. PCT/US2014/021624 on Mar. 7, 2014, now Pat. No. 9,925,054.

(Continued)

(51) Int. Cl.
*A61F 2/42* (2006.01)
*A61F 2/30* (2006.01)

(52) U.S. Cl.
CPC .. *A61F 2/4202* (2013.01); *A61F 2002/30205* (2013.01); *A61F 2002/30301* (2013.01);
(Continued)

(58) Field of Classification Search
CPC ............ A61F 2/4202; A61F 2002/4205; A61F 2002/4207
See application file for complete search history.

(56) References Cited

U.S. PATENT DOCUMENTS 3,872,519 A    3/1975 Giannestras et al.
3,987,500 A   10/1976 Schlein
(Continued)

FOREIGN PATENT DOCUMENTS

| DE | 3904004 A1 | 8/1990 |
|---|---|---|
| EP | 1731155 A2 | 12/2006 |
| WO | WO2006023824 A2 | 3/2006 |

OTHER PUBLICATIONS

Seale, Damani Y. Talus morphology and its functional implications on the ankle joint. Diss. Drexel University, 2011.

*Primary Examiner* — Brian A Dukert
(74) *Attorney, Agent, or Firm* — Mendelsohn Dunleavy, P.C.

(57) ABSTRACT

A prosthetic ankle including a talar component and a tibial component. At least a portion of top surface of the talar component has a convex curvature, relative to a location above the top surface, in the anterior to posterior direction as viewed in a sagittal plane cross-section, and a concave curvature relative to a location above the top surface, in the medial to lateral direction. An axis of cone projected based on medial and lateral circles located in medial and lateral sagittal plane cross-sections which approximate the average radius of curvature of the top surface of the talar component as viewed in medial and lateral sagittal plane cross-sections, has a total offset angle from the lateral direction in the range of 0° to 45°. In another aspect, the present invention further comprises a bearing component adapted for location between the tibial component and the talar component.

19 Claims, 17 Drawing Sheets

Related U.S. Application Data

(60) Provisional application No. 61/861,621, filed on Aug. 2, 2013, provisional application No. 61/789,090, filed on Mar. 15, 2013.

(52) U.S. Cl.
CPC ............... *A61F 2002/30576* (2013.01); *A61F 2002/30841* (2013.01); *A61F 2002/30879* (2013.01); *A61F 2002/4205* (2013.01); *A61F 2002/4207* (2013.01)

(56) References Cited

U.S. PATENT DOCUMENTS

| | | |
|---|---|---|
| 5,766,259 A | 6/1998 | Sammarco |
| 6,926,739 B1 | 8/2005 | O'Connor et al. |
| 7,025,790 B2 | 4/2006 | Parks et al. |
| 7,534,246 B2 | 5/2009 | Reiley et al. |
| 7,534,270 B2 | 5/2009 | Ball |
| 7,615,082 B2 | 11/2009 | Naegerl et al. |
| 7,713,305 B2 | 5/2010 | Ek |
| 7,799,077 B2 | 9/2010 | Lang et al. |
| 7,833,287 B2 | 11/2010 | Doddroe et al. |
| 9,750,613 B2 | 9/2017 | Petteys |
| 2005/0049711 A1 | 3/2005 | Ball |
| 2006/0020345 A1 | 1/2006 | O'Connor et al. |
| 2006/0142870 A1 | 6/2006 | Robinson et al. |
| 2010/0109326 A1 | 5/2010 | Sato et al. |
| 2010/0305572 A1 | 12/2010 | Saltzman et al. |
| 2011/0066245 A1 | 3/2011 | Lang et al. |
| 2012/0271430 A1 | 10/2012 | Arnett et al. |
| 2017/0181861 A1 | 6/2017 | Terrill et al. |
| 2017/0340450 A1 | 11/2017 | Toro Arbelaez et al. |

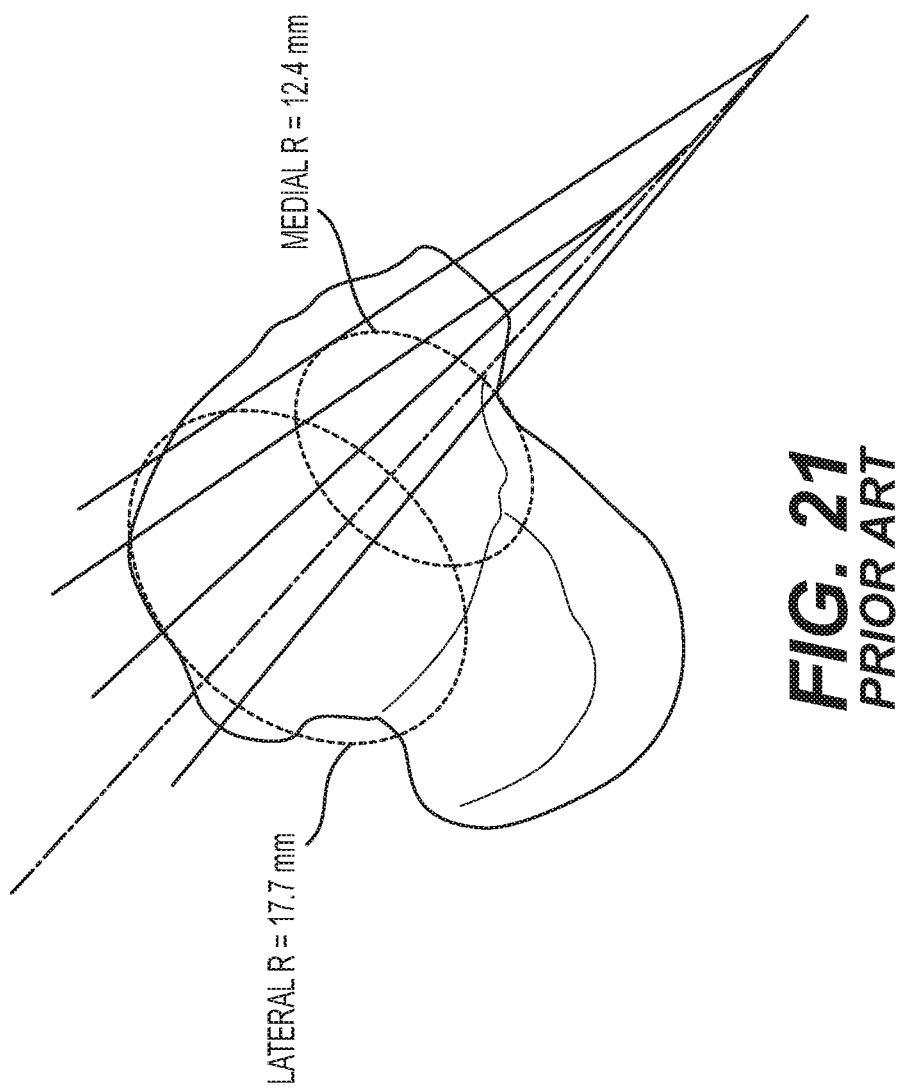

PROSTHETIC ANKLE

RELATED APPLICATION DATA

This application is a continuation of U.S. patent application Ser. No. 14/772,346, filed on Sep. 2, 2015, which, in turn, is a 371 continuation of International Application No. PCT/US2014/021624, filed Mar. 7, 2014, which, in turn, claims the benefit of U.S. Provisional Application No. 61/861,621, filed Aug. 2, 2013 and U.S. Provisional Application No. 61/789,090, filed Mar. 15, 2013, the entire disclosures of which are hereby incorporated by reference as if set forth fully herein.

BACKGROUND OF THE INVENTION

1. Field of the Invention

The present invention relates generally to prosthetic ankle implants. In particular, it is directed to a total ankle prosthesis device having a plurality of components that resemble the natural geometry of a human ankle.

2. Description of the Related Technology

For many years there has been considerable interest and activity with respect to ankle joint replacement, in which the degenerative articular surfaces are removed and replaced with an artificial joint called an ankle joint prosthesis, as a viable approach to the treatment of diseased or injured ankle joints. As the population ages, the demand for ankle joint prostheses is growing.

Fusion has long been an alternative to ankle arthroplasty. Fusion has its drawbacks. For example, there is a loss of motion in the ankle joint which may cause difficulties with other associated parts of the foot and leg. More recent research on the ankle joint has allowed for improved designs for ankle joint prostheses and better implant materials allowing ankle joint prostheses to dramatically improve in quality and longevity. Many types of ankle joint prostheses have been developed over the past thirty years.

U.S. Pat. No. 6,409,767 discloses an ankle joint prosthesis comprising a talus implant for implanting in or on the talus and a top element including a tibia implant for implanting in or on the base of the tibia. The top element and the talus implant are mounted to move relative to each other by friction on a contact interface so as to allow the ankle to move. The contact interface presents a friction surface that can be considered a portion of a substantially frustoconical surface. When implanted, the substantially frustoconical surface is oriented so that its larger radius portion is directed substantially towards the lateral side of the ankle in accordance with the postulate of Inman's Joints. The top surface of the talar implant has two ribs on both edges running from the anterior to the posterior edges.

One example of an ankle joint prosthesis is disclosed in U.S. Pat. No. 7,025,790, which describes an ankle joint prosthesis comprising tibial, talar and mobile or semi-constrained bearing components that may be implanted in a patient. The top surface of the tibial component has a convex curvature and is configured so as to approximate and match with the curvature of a prepared portion of the distal tibia. The bottom surface of the tibial component is approximately flat. The top surface of the talar component has a saddle-shaped, convex curvature in its anterior to posterior plane. The bottom surface of the talar component has a concave curvature and is configured so as to approximate and match with the curvature of a prepared portion of the talus.

*Inman's Joints of the Ankle*, second edition, Chapter 2, "Functional Morphology of the Trochlea," pp. 7-13, Ed. James B. Stiehl, M.D., *Williams and Wilkins* (1991) (hereinafter "Inman's Joints"), postulates that the trochlea of the talus is a section of a frustrum of a cone whose apex is directed medially and whose apical angle varies considerably from individual to individual. Many of the prior art devices are based on this postulate. However, the present device is based on a different postulate, namely that the talus is a section of a frustrum of a cone whose apex is directed substantially in a lateral direction rather than in a medial direction. This type of device is characterized by a medial curvature larger than the lateral curvature as viewed in sagittal plane cross-sections.

WO 2006/023824 discloses an ankle joint prosthesis including a talar component having a lower surface with a bone fixation portion for fixation to the talus and an upper surface designed for articulation using a bearing component. The bearing component can have a lower surface for articulation relative to the talar component and an upper surface for articulation relative to the tibial component. The tibial component can have a lower surface for articulation relative to the bearing component and an upper surface with a bone fixation portion for fixation to the tibia and/or fibula. The talar component has height greater on the lateral side than on the medial side.

U.S. Pat. No. 7,615,082 discloses an artificial joint, particularly for replacing a talocrural joint, including a first primary joint surface that forms an articular fossa for replacing the tibia and having concave curvature extending parallel to a primary functional plane of the joint, which corresponds to the sagittal plane, and a second primary joint surface which cooperates with the first primary joint surface as a component of a condoyle that replaces the talus and has convex curvature on the primary functional plane that is adapted to the first primary joint surface. The radius of the second primary joint surface decreases from the lateral side to the medial side of the joint in accordance with the postulate of Inman's Joints.

After initial encouraging results, follow-up clinical studies on many of these ankle joint prostheses revealed frequent failures of such implants due mainly to the inadequate restoration of the natural mobility and the poor stability of the resulting ankle implants. Many of the problems originated from our poor understanding of the relative contribution of the ligamentous structures and functional morphology of the articular surfaces in providing passive and active stability for the human ankle joint.

One objective of the present invention is to provide an improved prosthetic ankle that more closely approximates the natural geometry of the articulating bones in the ankle joint. The ankle prosthesis will allow mobility characteristics that more closely resemble the movement of a natural ankle than many prior art devices.

SUMMARY OF THE INVENTION

In one aspect, the present invention is directed to a prosthetic ankle comprising a talar component and a tibial component, wherein at least a portion of top surface of the talar component has a convex curvature relative to a location above the top surface, in the anterior to posterior direction as viewed in a sagittal plane cross-section, a concave curvature relative to a location above the top surface, in the medial to lateral direction as viewed in a frontal plane cross-section, and an average radius of curvature of at least a major portion of the medial side of the top surface of the talar component that is larger than an average radius of curvature of at least a major portion of the lateral side of the top surface of the talar component as viewed in sagittal plane cross-sections on the lateral and medial sides.

In another aspect, the present invention further comprises a bearing component adapted for location between the tibial component and the talar component.

In yet another aspect, the present invention provides a prosthetic ankle wherein the lateral to medial curvature of the top surface of the talar component varies from the lateral side to the medial side.

In yet another aspect, the present invention provides a prosthetic ankle wherein the average radius of curvature of the top surface of the talar component varies from a location proximate to the posterior end of the talar component to a location proximate to the anterior end of the talar component, as viewed in frontal plane cross-sections.

In yet another aspect, the present invention provides a prosthetic ankle having surfaces specially adapted for attachment with the adjoining tibia and talus.

In yet another aspect, the present invention provides a prosthetic ankle with different levels of constraint, ranging from unconstrained to semi-constrained.

In yet another aspect, the present invention provides a prosthetic ankle with a bottom surface of a tibial component and the top surface of a bearing component that are both flat.

In yet another aspect, the present invention relates to a prosthetic ankle including a tibial component having a top surface for location adjacent to a tibia and a bottom surface; and a talar component having a bottom surface for location adjacent to a talus, and a top surface. The top surface of the talar component includes a convex curvature relative to a location above the top surface, in an anterior to posterior direction as viewed in a sagittal plane cross-section, and a concave curvature relative to a location above the top surface, in a medial to lateral direction as viewed in a frontal plane cross-section. An axis of cone projected based on medial and lateral circles located in medial and lateral sagittal plane cross-sections which approximate the average radius of curvature of the top surface of the talar component as viewed in medial and lateral sagittal plane cross-sections, has a total offset angle from the lateral direction in the range of 0° to 45°.

BRIEF DESCRIPTION OF THE DRAWINGS

FIG. 21 depicts a cone generated by a surface that is tangent to each of the circles of FIGS. 19-20.

DETAILED DESCRIPTION OF THE PREFERRED EMBODIMENT(S)

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

All references to frontal plane cross-sections are to be interpreted as references to coronal plane cross-sections as these terms are used interchangeably in the present application.

Figure 1:
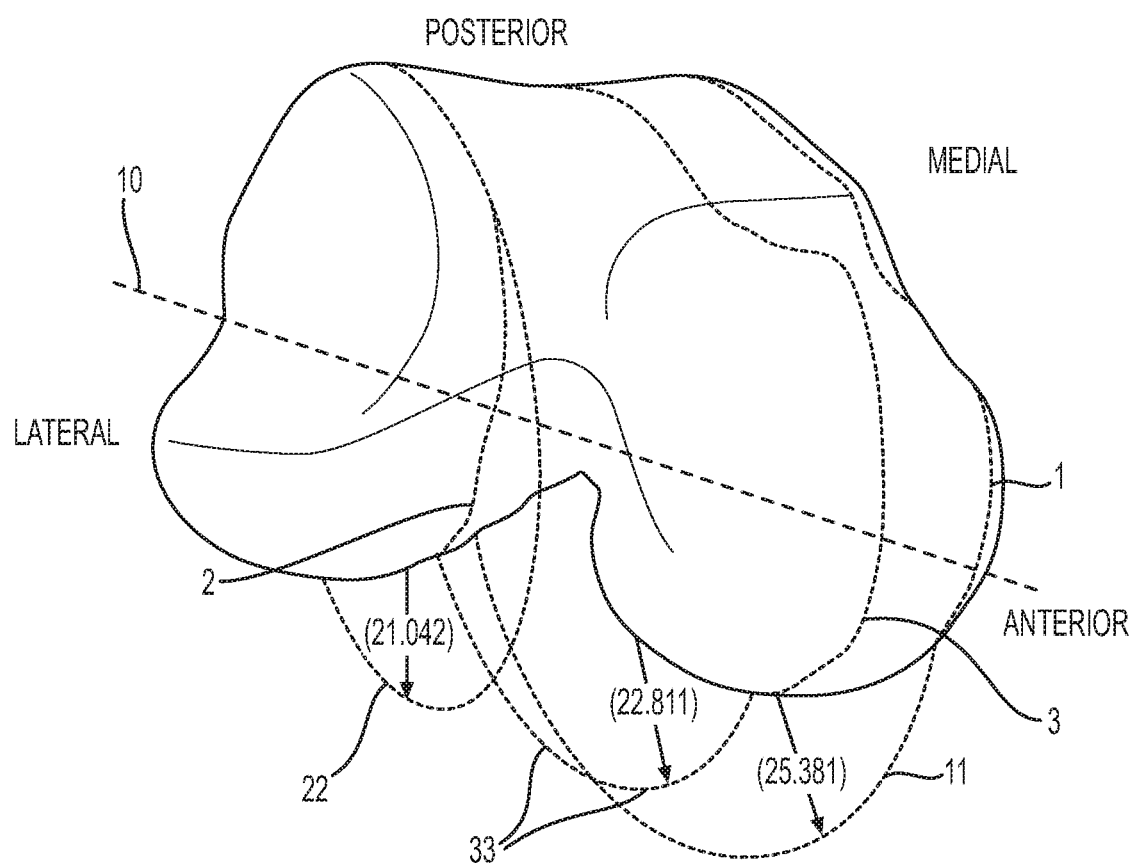
FIG. 1 depicts a human talus and identifies the lateral and medial sides as well as the anterior and posterior directions as used in the description of the present application.

Referring to FIG. 1, there is shown a human talus. The anterior is the front end of the talus in the direction of the toes. The posterior is the back end of the talus in the direction of the heel. The lateral side refers to the outside of the talus of a foot or an ankle, i.e. the side that faces away from the other foot or ankle. The medial side refers to the inside of the talus of a foot or an ankle, i.e. the side that faces toward the other foot or ankle. All references to orientation in this application are given based on the orientation of the prosthetic ankle when implanted in a human. References to the top or to above the device refer to a direction towards the head of a human whereas references to the bottom or below the device refer to a direction towards the bottom of the foot of a human.

Implantation of the device of the invention is typically done from the anterior side of the ankle. Prior to implantation of the prosthetic ankle, the lower surface of the tibia and the upper surface of the talus may be prepared to receive the device by, for example, shaping these surfaces to a desired, predetermined shape. For example, the curvature of each of the lower surface of tibia and the upper surface of talus may be adapted to receive a particular prosthetic ankle by, for example, shaping these surfaces to approximate the shape of adjacent surfaces of the tibial and talar components 100, 300 of the prosthetic ankle, respectively. Thus, the tibial component 100 may be adapted to fit snugly onto the shaped lower surface of the tibia and the talar component 300 may be adapted to fit snugly onto the shaped upper surface of the talus.

The tibial component 100 of the present invention is designed to be joined to the tibia during the implantation procedure using conventional joining means such as adhesives, screws, spikes, friction fit, form fit and/or any combination thereof. The talar component 300 of the present invention is designed to be jointed to the talus during the implantation procedure using conventional joining means such as adhesives, screws, friction fit, form fit, spikes, and/or any combination thereof.

In one aspect, the present invention relates to a prosthetic ankle including a tibial component 100 and a talar component 300. The talar component 300 according to the present invention is specially designed using the natural curvature and shape of the top surface of a human talus as a basis for the design elements of talar component 300.

The design of a talar component 300 of the present invention is described in relation to FIGS. 1-6. Initially, three sagittal plane cross-sections are employed to model key aspects of the upper surface of the talus. Referring to FIG. 1, the three sagittal plane cross-sections are shown as the medial plane 1, the lateral plane 2, and the central plane 3.

The medial plane 1 is a sagittal plane cross-section taken on the medial side of the talus that passes through the peak of the medial talar trochlear shoulder. The medial plane 1 should follow the peak of the shoulder from anterior to posterior. The peak of the medial talar trochlear shoulder is defined as the point of inflection.

Figure 2:
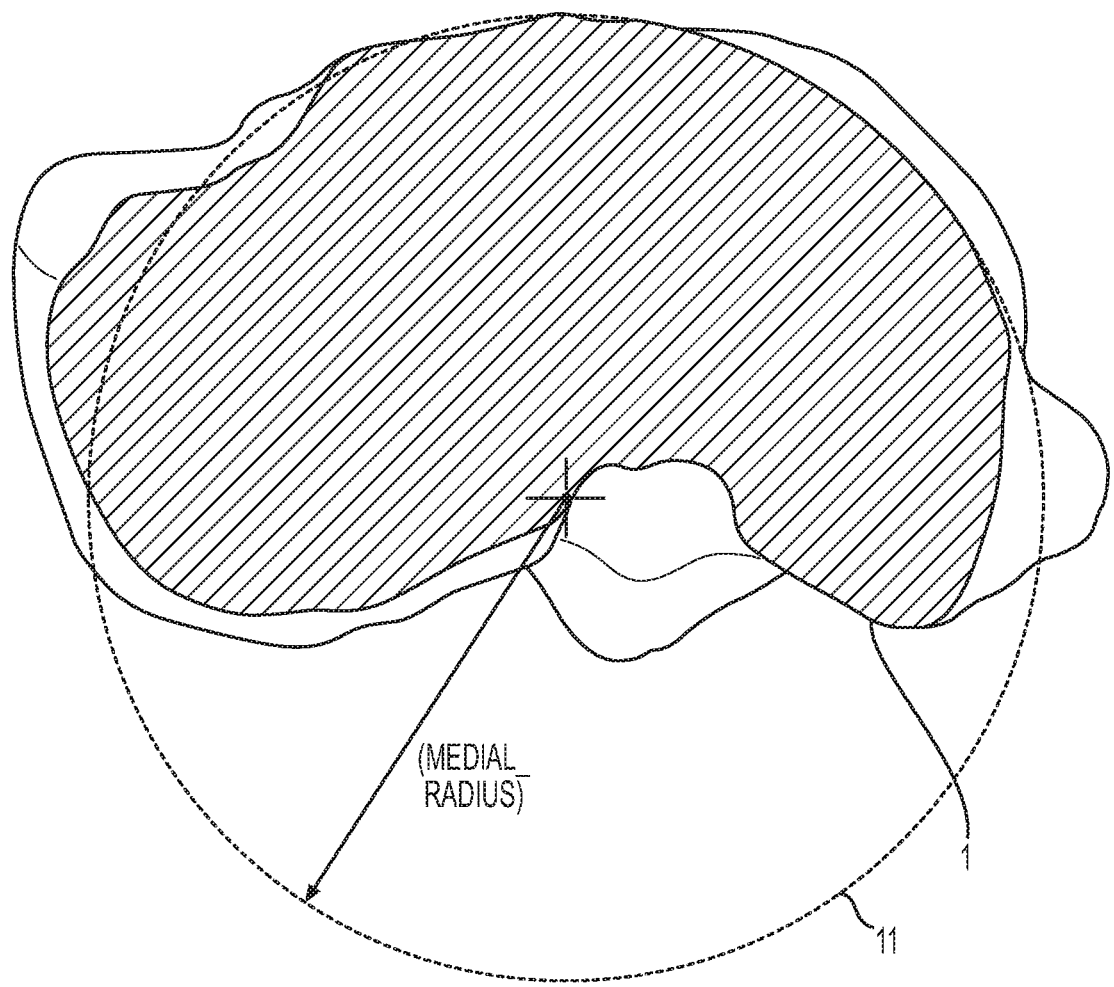
FIG. 2 is a sagittal plane cross-section of a talus on the medial side taken along medial plane 1 of FIG. 1, shown with a medial circle that represents a best fit to the radius of curvature of the top surface of the talus shown in the cross-section taken in medial plane 1.

The cross-section of the talus bone at the medial plane 1 is shown in FIG. 2. The top portion of the cross-section shows the top surface curvature of the talus from the posterior end to the anterior end. In the next step of the process, a circle is best fit to at least a major portion of the top surface curvature of the talus in medial plane 1 to define a medial circle 11. The average measured radius of this medial circle 11 for a sampling of adult human tali was about 25.38 mm.

The sagittal plane cross-section used for the lateral plane 2 is located by first creating a plane that is parallel to the medial plane 1 with an offset from the medial plane 1 in the lateral direction. The offset should approximate the distance between the lateral trochlear shoulder and the medial plane 1. A suitable average lateral plane offset starting from medial plane 1 may be about 25 mm but can range from 20-30 mm, depending on the patient. The lateral plane 2 is then rotated about a projected superior-inferior line such that the resultant lateral plane 2 follows the peak of the lateral trochlear shoulder from an anterior location to a posterior location. A typical rotation of lateral plane 2 is from about 7-12 degrees with the average rotation being about 9.9 degrees.

Figure 3:
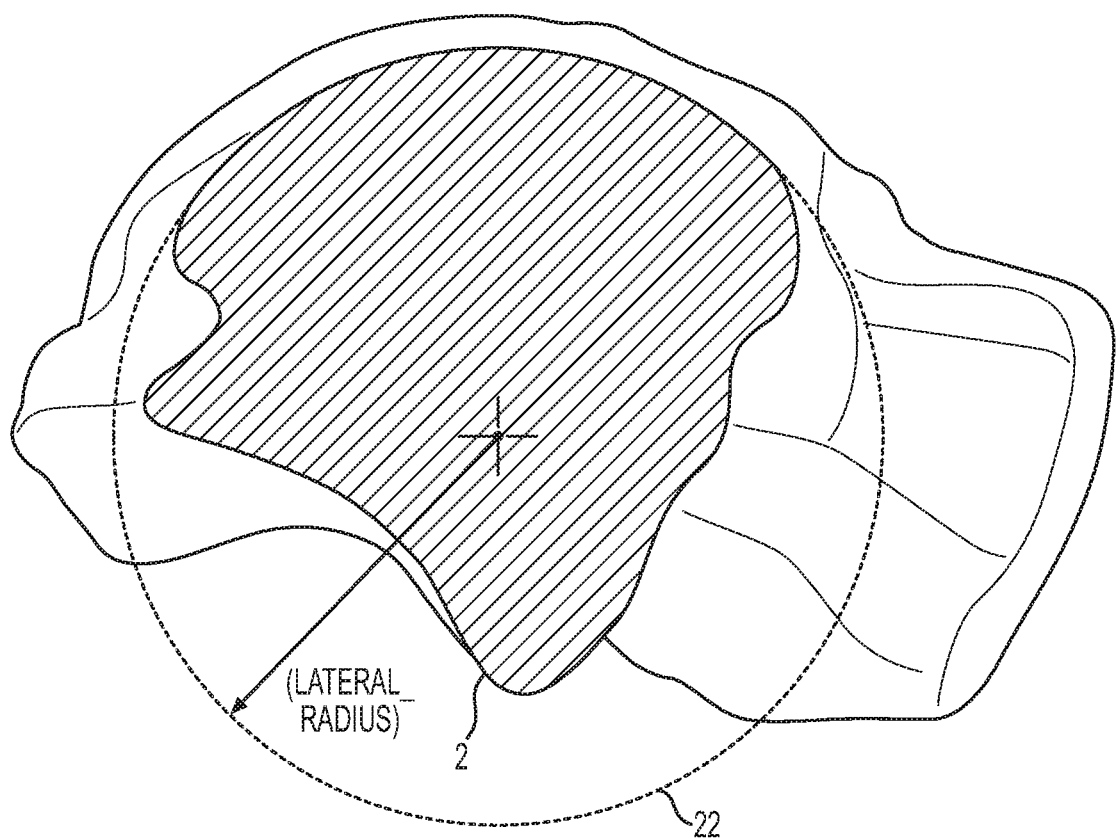
FIG. 3 is a sagittal plane cross-section of a talus on the lateral side taken along lateral plane 2 of FIG. 1, shown with a lateral circle that represents a best fit to the radius of curvature of the top surface of the top surface of talus shown in the cross-section taken in lateral plane 2.

The cross-section of the talus bone at the lateral plane 2 is shown in FIG. 3. The top portion of the cross-section at the lateral plane 2 shows the top surface curvature of the talus from the posterior end to the anterior end as viewed in this sagittal plane cross-section. A circle is best fit to at least a major portion of the top surface of the lateral plane 2 to define a lateral circle 22. The average measured radius of the lateral circle 22 of a sampling of several adult human tali was about 21.04 mm.

The central plane 3 is located by first creating a plane that is parallel to the medial plane 1 with an offset from medial plane 1 in a lateral direction. The offset should approximate the change in curvature along the central portion of the trochlear surface from anterior to posterior. A suitable average central plane offset starting from medial plane 1 is about 10.5 mm and may vary from about 9-12 mm. Then this plane is rotated about the projected superior-inferior line such that the resultant central plane 3 follows the trough or valley of the medial to lateral concavity in the anterior to posterior direction. A typical rotation of central plane 3 is from about 1-7 degrees with the average rotation being about 4 degrees.

Figure 4:
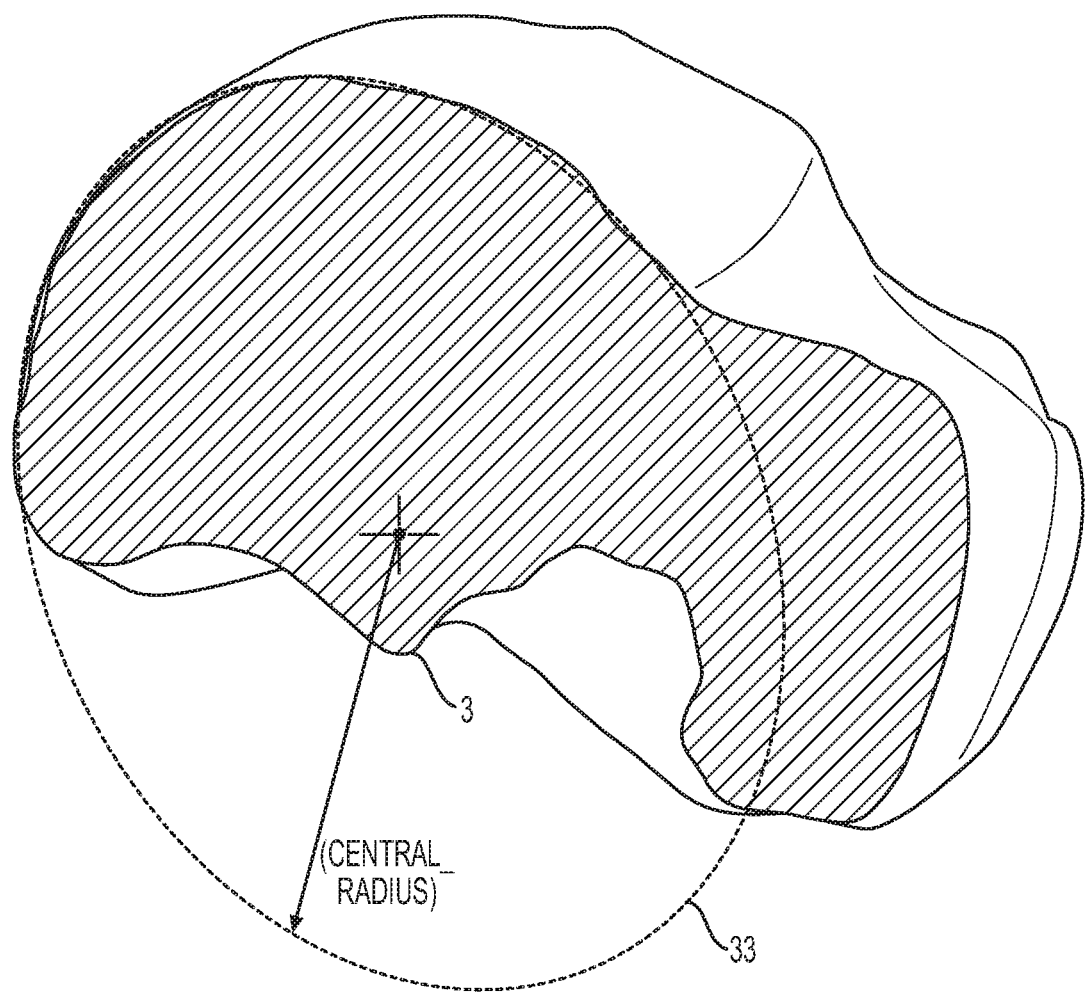
FIG. 4 is a sagittal plane cross-section of a talus at a central location taken along central plane 3 of FIG. 1, shown with a central circle that represents a best fit to the radius of curvature of the top surface of the talus shown in the cross-section taken in the central plane 3.

The cross-section of the talus bone at the central plane 3 is shown in FIG. 4. The top portion of the cross-section shows the curvature of the top surface of the talus from the posterior end to the anterior end as viewed in this sagittal plane cross-section. A circle is best fit to at least a major portion of the top surface curvature at the central plane 3 cross-section to define a central circle 33. The average radius of the central circle 33 was about 22.81 for a sampling of several adult human tali.

Figure 5A:
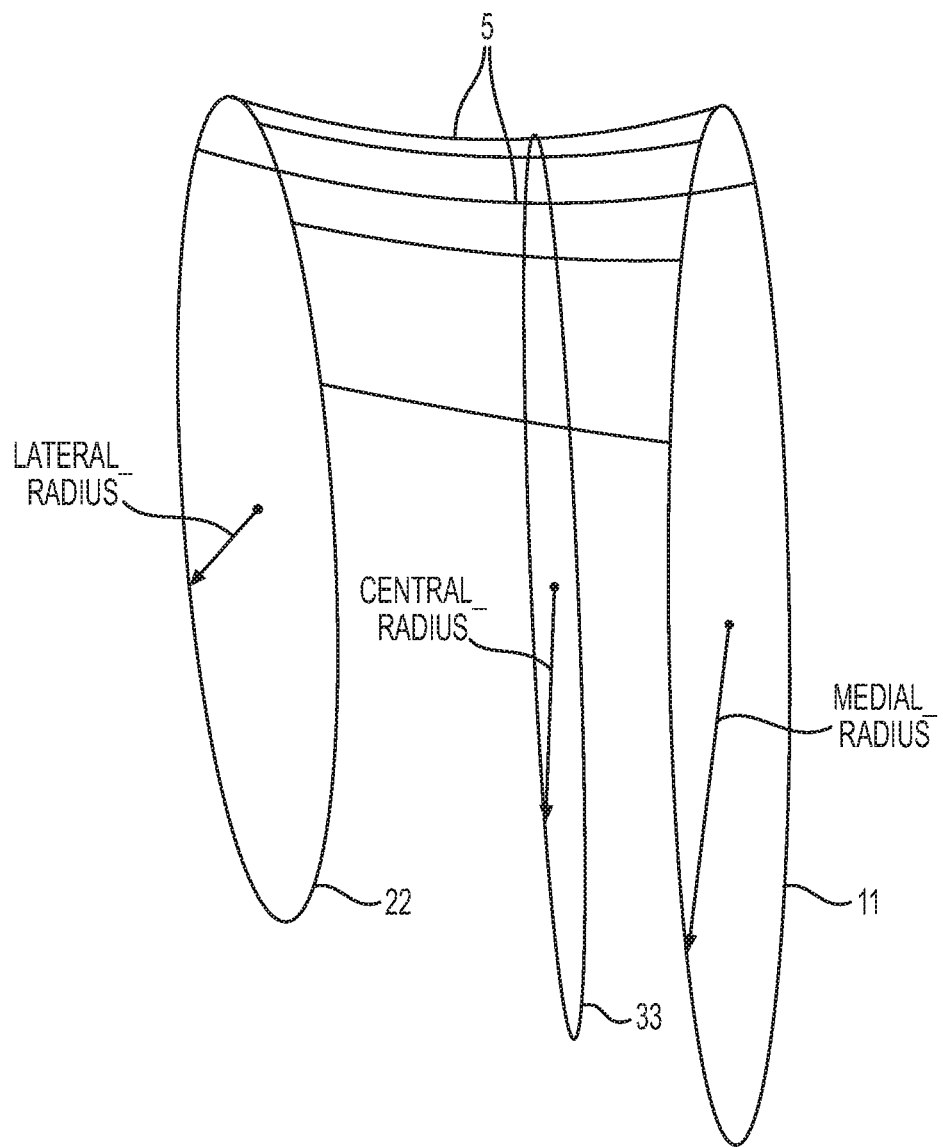
FIG. 5A depicts the medial circle, lateral circle and central circle of FIGS. 2-4 that are used to model the top surface of the human talus showing the radius of each of the circles.
Figure 5B:
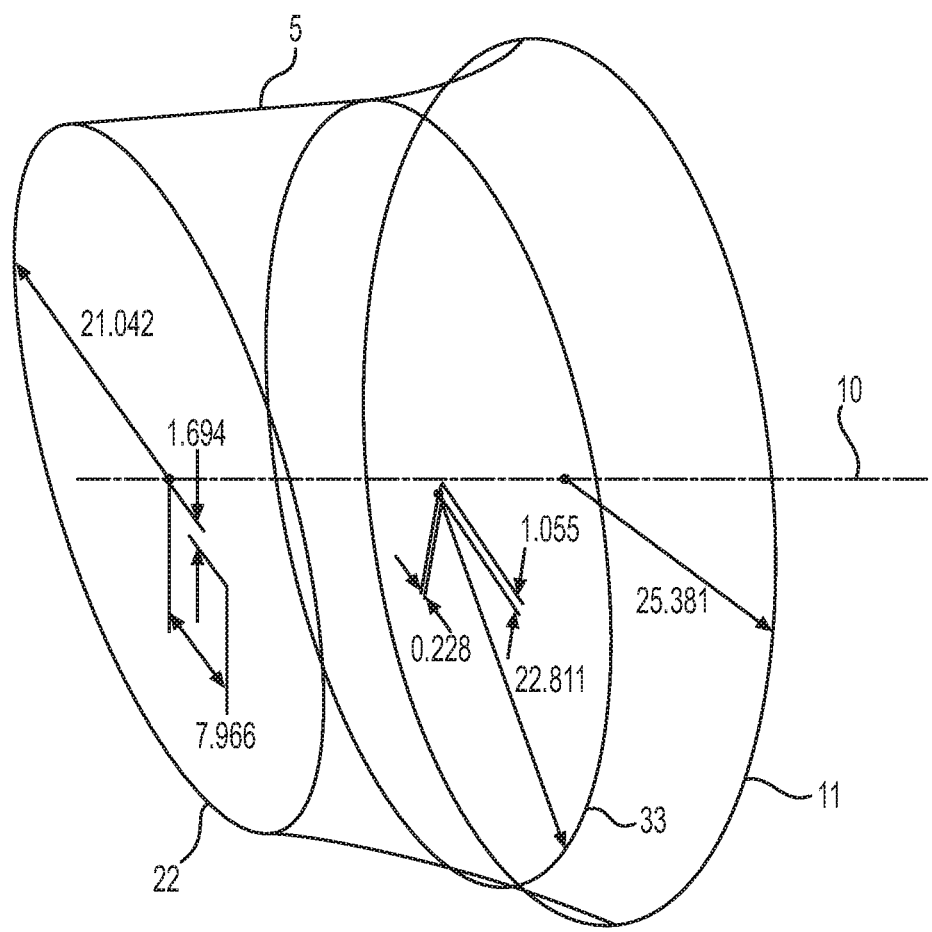
FIG. 5B depicts a conical surface used to model the talus and which is formed using the medial, lateral and central circles shown in FIG. 5A.
Figure 6:
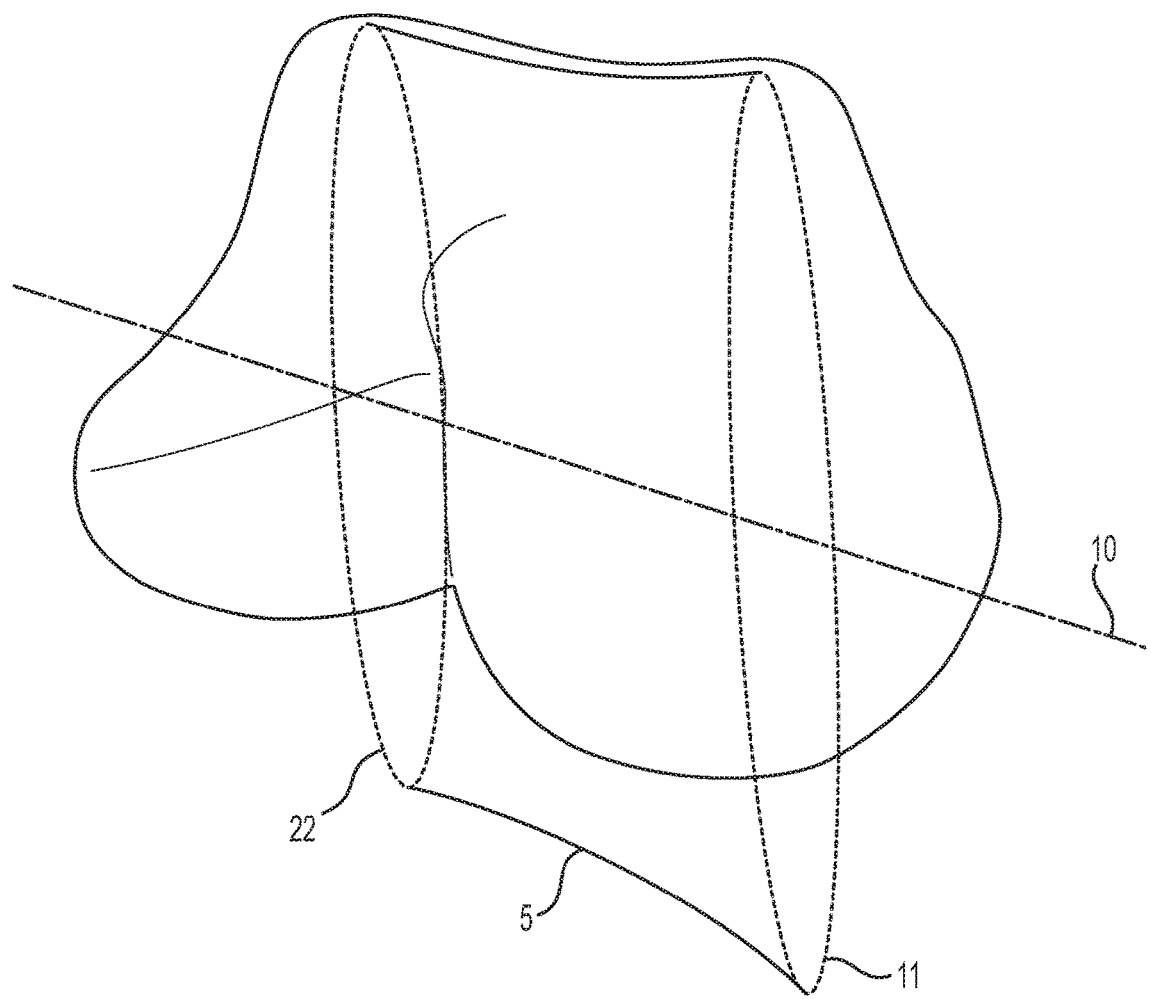
FIG. 6 shows the conical surface of FIG. 5B superimposed on a human talus.
Figure 7:
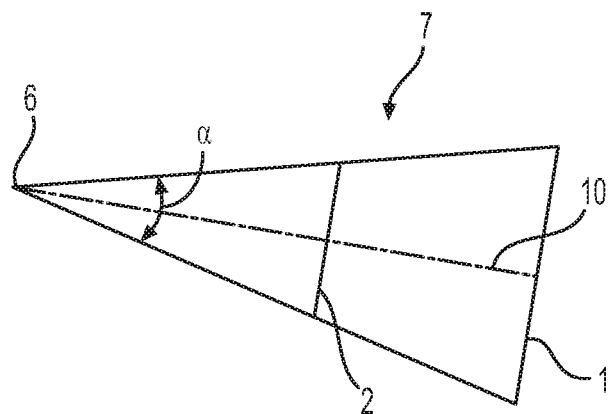
FIG. 7 shows a cone that the present invention uses to model a human talus.

Referring to FIGS. 5A and 5B, the medial circle 11, lateral circle 22 and central circle 33 are used to model the top surface of a human talus. Thus, in FIG. 5A, the top portions of the three circles are connected to form a frustoconical surface that models the top surface of the human talus. Connections in five frontal plane cross-sections are shown in FIG. 5A. In FIG. 5B, the bottom surfaces of the medial circle 11, lateral circle 22 and central circle 33 are connected to form a truncated cone 5 that approximates the human talus. FIG. 6 shows the truncated cone 5 of FIG. 5B superimposed on a human talus. The truncated cone 5 of FIGS. 5B and 6 can be extended to generate a full cone 7 as shown in FIG. 7. The apex 6 of the cone 7 points in a substantially lateral direction due to the fact that the radius of the medial circle 11 is larger than the radius of the lateral circle 22, as described in greater detail below.

As shown in FIG. 6, a line drawn through the center of the medial circle 11 and the center of lateral circle 22 defines the medial-lateral axis 10 of both the truncated cone 5 and the full cone 7. Referring to FIG. 7, the cone 7 intersects with the medial plane 1 and lateral plane 2. The apex angle alpha of this cone 7 may be in the range of from 2° to 30°, or from 3° to 20°, or from 5° to 10°.

Figure 17:
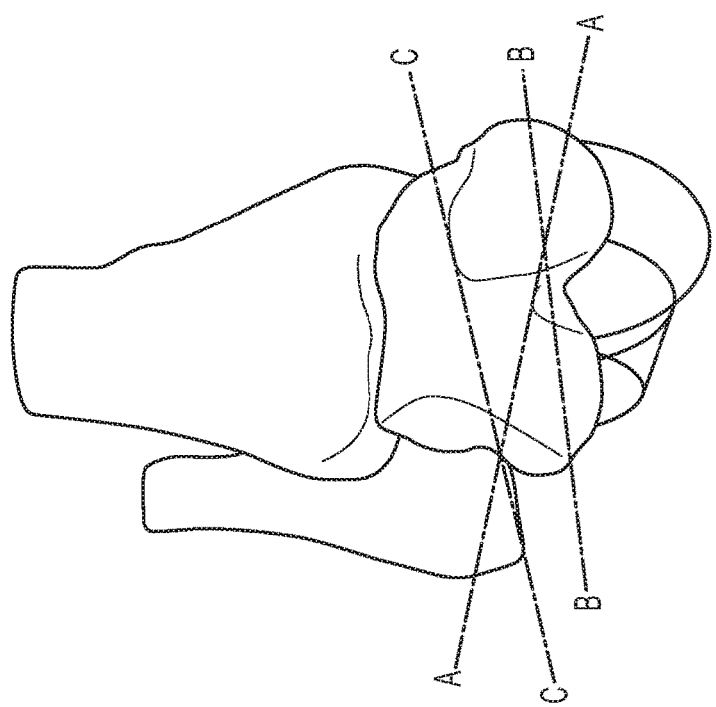
FIG. 17 shows an alternative model for defining a conical surface used to describe the top surface of the talus.

Referring to FIG. 17, the talus may also be described using an alternative model. Line A-A of FIG. 17 connects the centers of the medial circle 11 and lateral circle 12, considered as the axis 10 of the cone 7 that resembles the top surface of the talus. Line B-B is a line perpendicular to the medial circle 11 and through its center. Line C-C is a line connecting the tips of the medial and lateral malleoli. In this alternative model, the angle between lines A-A and B-B, which is called total axis offset angle, is in a range from 0° to 40°, or from 5° to 35°, or from 10° to 30°, or from 16° to 24°. This angle when projected onto a coronal plane, which is called coronal axis offset angle, is in a range of from 0° to 38°, or from 6° to 32°, or from 10° to 28°, or from 15° to 23°. The angle between lines A-A and B-B when projected onto a transverse plane, which is called transverse axis offset angle, is in a range of from 0° to 20°, or from 4° to 16°, or from 6° to 14°. Further, the angle between line A-A connecting the centers of the medial circle 11 and lateral circle 12 and line C-C connecting the tips of the medial and lateral malleoli, is in a range from 5° to 25°, or from 10° to 20°, or from 13° to 20°.

Figure 9:
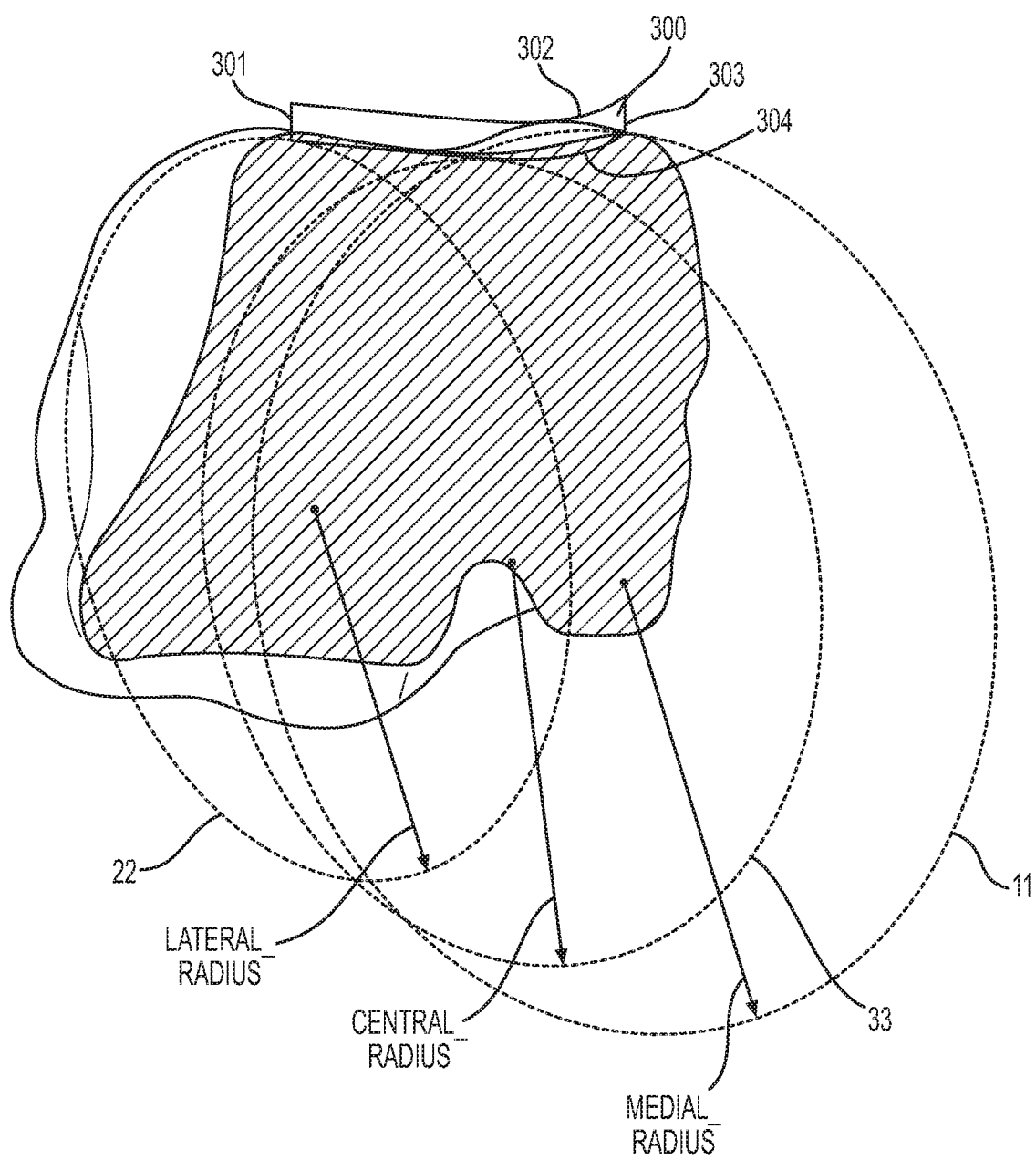
FIG. 9 shows a frontal plane cross-sectional view of a talar component in accordance with one embodiment of the invention fit on top of a human talus.
Figure 10:
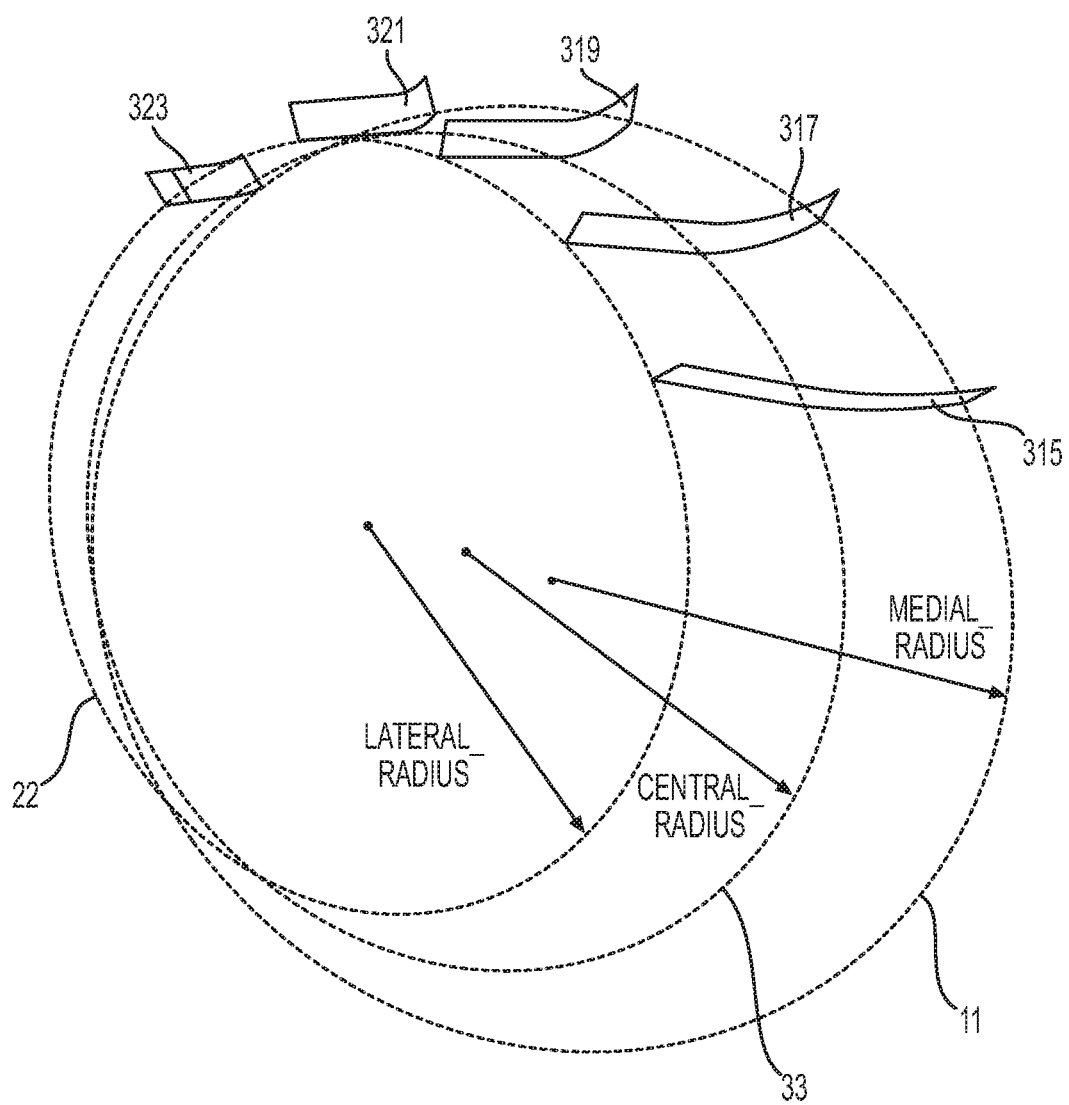
FIG. 10 shows multiple frontal plane cross-sectional views of a talar component in accordance with one embodiment of the invention.
Figure 11:
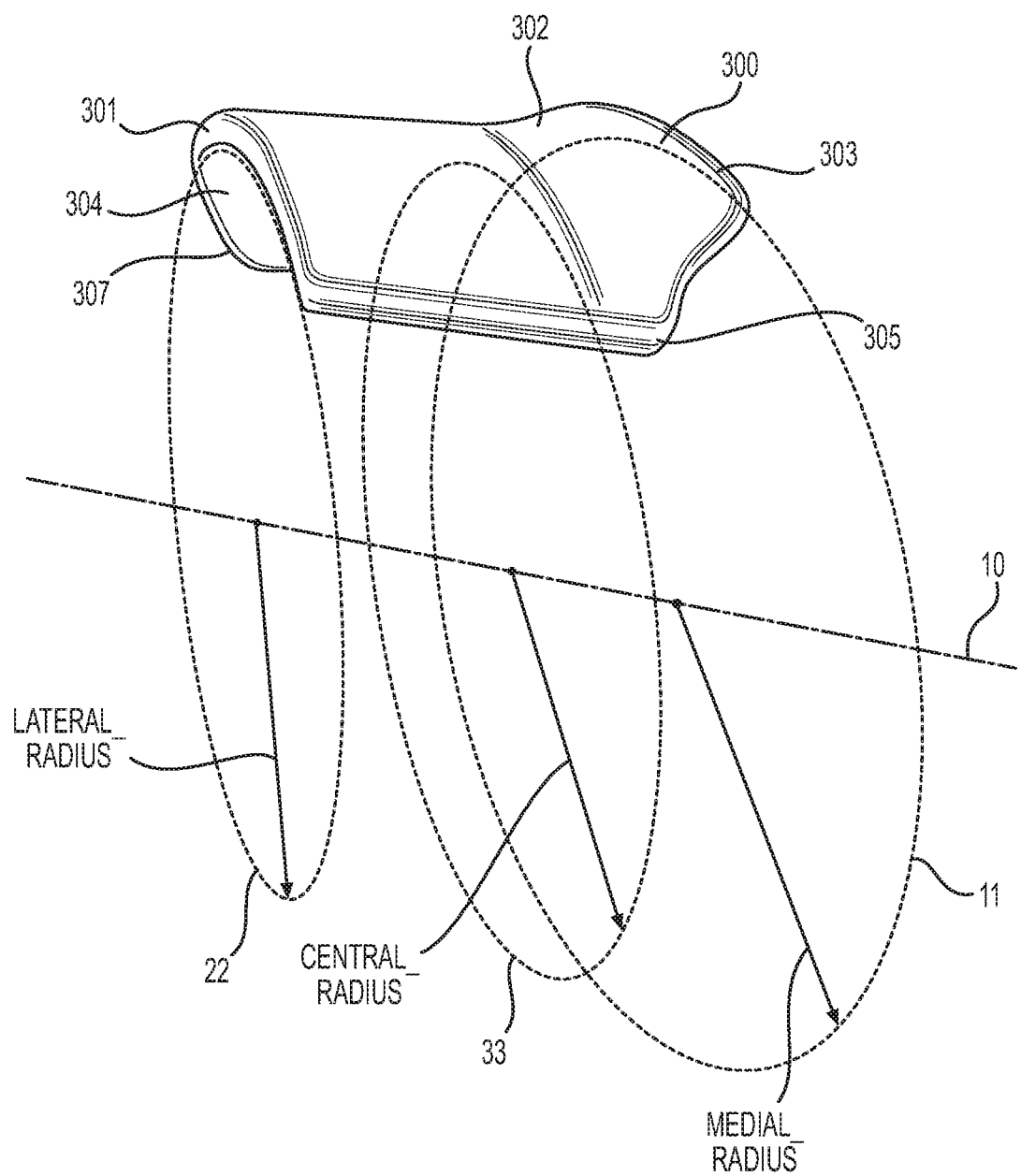
FIG. 11 shows a top perspective view of one embodiment of a talar component fitted onto the frustoconical surface of FIGS. 5A-5B and 6 which models a top surface of the human talus.

The talar component 300 of the prosthetic ankle of the present invention has a top surface 302 that preferably resembles certain contours of the top surface of the talus. Referring to FIG. 9, the talar component 300 of the present invention may be designed by generating frontal plane cross-sections of the talar component 300 in one or more frontal planes following the curvature of the top surface of the truncated cone 5 obtained as described above using the medial circle 11, lateral circle 22 and central circle 33. Five different frontal plane cross-sections 315, 317, 319, 321 and 323 of the talar component 300 are shown in FIG. 10. Cross-section 315 is the anterior-most cross-section and cross-section 323 is the posterior-most cross-section. These cross-sections 315, 317, 319, 321 and 323 may be connected to form a talar component 300 as shown in FIG. 11.

In some embodiments, the top surface 302 of the talar component 300 may have a larger curvature on the medial side 303, as compared with the curvature on the lateral side 301, as viewed in a frontal plane cross-section. As shown in FIG. 9, the top surface 302 on the lateral side 302 of talar component 300 may be flat or almost flat. In some other embodiments, the curvature of the top surface 302 of talar component 300, as viewed in a frontal plane cross-section may be uniform or substantially uniform from the medial side 303 to the lateral side 301. In some cases, the frontal-plane curvature in the cross-section taken proximate to posterior end 307 may change from concave to convex relative to a location above top surface 302.

The curvature of the top surface 302 of talar component 300 as viewed in a frontal plane cross-section may be described by a creating a frontal plane circle with its center located above top surface 302 and which is best fit to the curvature of the top surface 302. The radius of such a best fit frontal plane circle may vary in different frontal plane cross-sections 315, 317, 319, 321 and 323 of the talar component 300. In some embodiments the radius of the frontal plane circle is smaller when measured in a frontal plane proximate to the anterior end 305 of the talar component 300 than the radius of the frontal plane circle when measured proximate to the posterior end 307 of the talar component 300. A larger radius of the frontal plane circle corresponds to less curvature in that frontal plane.

In some embodiments, the radius of such a best fit frontal plane circle taken proximate to the anterior end 305 of talar component 300 may be in the range of 24 mm to 180 mm, or 35 mm to 165 mm, or from 50 to 150 mm. The radius of such a best fit frontal plane circle taken at a central location between the anterior end 305 and the posterior end 307 of the talar component 300 may be in the range of 25 mm to 300 mm, or from 40 mm to 280 mm, or from 60 mm to 250 mm. The radius of such a best fit frontal plane circle taken proximate to the posterior end 307 of talar component 300 may be in the range from 25 mm to infinity, or from 40 mm to infinity, or from 60 mm to infinity. When the radius of the best fit frontal plane circle is infinite, this indicates that the top surface 302 is flat or changes from concave curvature to convex curvature, relative to a location above top surface 302, as viewed in that frontal plane cross-section.

Referring to FIG. 10, five frontal plane cross-sections of the talar component 300 are shown. From a comparison of the cross-section taken at the posterior end 307 of talar component 300 and the cross-section taken at the anterior end 305 of talar component 300 it can be seen that in the depicted embodiment of the invention the top surface 302 of talar component 300 has the most curvature at the anterior end 305 of talar component 300 and has less curvature at the posterior end 307 of talar component 300. At the posterior end 307, top surface 302 of talar component 300 may be flat or substantially flat, as viewed in a frontal plane cross-section. Relative to a location above top surface 302 of talar component 300, the curvature in these frontal plane cross-sections is concave.

This variation of the average radius of concave curvature of top surface 302 in the anterior posterior direction is used to more closely approximate the actual shape of the talus of a subject since a variation in average radius of curvature is also present in the human talus. As a result, this feature may provide a closer approximation of the actual motion of an ankle relative to a prosthetic ankle without this feature. This feature can help to provide stability and smooth motion in inversion and eversion.

As shown in FIG. 11, talar component 300 has a top surface 302 that resembles certain aspects of the modeled top surface of the talus. Of the three circles 11, 22, 33 that are used model the top surface 302 of the talar component 300, the radius of the medial circle 11 is larger than the radius of the lateral circle 22. The ratio of the radius of medial circle 11 to the radius of lateral circle 22 may be in the range of about 1.5:1 to 1.01:1, or from 1.35:1 to 1.1:1, or from 1.3:1 to 1.15:1. In one embodiment, the ratio of the radius of the medial circle 11 to the radius of the lateral circle 22 is about 1.25:1-1.2:1.

It is not necessary to take actual measurements of the human talus to develop the circles 11, 22 and 33. Rather, these circles can be developed from the information provided herein rather than by actual measurement. In practice, it may be advantageous to provide different sizes of implants that can be selected for particular patients or, the technique of the present invention can also be used to make customized implants tailored to specific patients by taking actual measurements of the patient's ankle.

Talar component 300 of one embodiment of the invention has a saddle-shaped structure that has curvature on both its top surface 302 and bottom surface 304. Top surface 302 has convex curvature relative to a location above the top surface, in the direction from anterior end 305 to posterior end 307 as viewed in a sagittal plane cross-section and concave curvature relative to a location above the top surface, in the direction from lateral side 301 to medial side 303, as viewed in a frontal plane cross-section, which, in combination form the saddle shape of top surface 302 of talar component 300.

The convex curvature of top surface 302 in the medial plane 1 has a larger average radius of curvature than the average radius of curvature of the convex curvature of top surface 302 in the lateral plane 2 of the talar component 300 as indicated by the fact that the radius of the lateral circle 22 is smaller than the radius of the medial circle 11. The top surface 302 of talar component 300 thus resembles a truncated conical surface oriented so that the cone has its apex on the lateral side 301 of the ankle. The top surface 302 of the talar component 300 thus approximates the native truncated conical surface shape of the trochlear surface of the talus.

The average radius of curvature of the top surface 302 in a sagittal plane cross-section is obtained by averaging the radius of curvature over a major portion of the top surface 302 of the talar component 300 in a sagittal plane, which major portion constitutes from at least greater than half of the length of the top surface 302 to the entire length of the top surface 302 of the talar component 300 in the anterior/posterior direction, or alternatively at least 80% of the length of the top surface 302 or at least 90% of the length of the top surface 302 of the talar component 300 in the anterior/posterior direction.

The particular curvature of the top surface 302 of talar component 300 of the present invention provides significant benefits relative to existing prior art devices. For example, the provision of an average radius of concave curvature of the top surface 302 on the medial side 303 of the talar component 300 that is larger than the average radius of concave curvature on the lateral side 301 of the talar component 300, as viewed in a sagittal plane cross-section, provides a shape of a truncated conical surface with the apex of the cone oriented in a substantially lateral direction. As a result, the device of the present invention allows motion that closely resembles supination and allows an approximation of the movement of an actual ankle, particularly in the lateral and medial directions as well as in plantar flexion.

A result of these features of the present invention is the provision of a prosthetic ankle wherein the truncated conical shape 5 used to approximate the talus can be extended to provide a cone 7 with the apex 6 oriented substantially in a lateral direction. By "substantially in a lateral direction" is meant that the apex 6 of the cone 7 may be oriented at an angle from the lateral direction. As a result, the talar component 300 of the present invention can be fabricated to ensure that the device is oriented similarly to the actual talus of a particular subject or based on information obtained from several subjects.

In certain embodiments, axis 10 of cone 7 is skewed upward and/or in the anterior direction, relative to the lateral direction. The angle between axis 10 and the lateral direction, as viewed in three dimensions, is referred to as the total conic offset angle, which may be in the range of 0° to 45°, or 3° to 40°, or 7° to 38°.

The angle between the axis 10 and the lateral direction when projected in an horizontal plane, is referred to as the horizontal conic offset angle, which may be in the range of from 0° to 35°, or from 3° to 30°, or from 5° to 28°.

The angle between axis 10 and the lateral direction when projected in a vertical plane, is referred to as the vertical conic offset angle, which may be in the range of from 0° to 40°, or from 3° to 37°, or from 5° to 35°.

In certain embodiments, the top surface 302 of the talar component 300 may resemble a truncated cone 7 having an axis 10 along line A-A of FIG. 17, and being further defined by line B-B extending perpendicular to the medial circle 11 of the cone and through the center of the medial circle 11 (FIG. 17). In this embodiment, cone 7 represents the top surface of the talar component 300 and has a total axis offset angle in a range from 0° to 40°, or from 5° to 35°, or from 10° to 30°, or from 16° to 24°. The coronal axis offset angle is in a range of from 0° to 38°, or from 6° to 32°, or from 10° to 28°, or from 15° to 23°. The transverse axis offset angle is in a range of from 0° to 20°, or from 4° to 16°, or from 6° to 14°.

The bottom surface 304 of talar component 300 preferably has a concave curvature in the anterior to posterior direction, as viewed in a sagittal plane cross-section from a location below bottom surface 304. The concave curvature is designed to be suitable for implantation onto the talar dome. However, a skilled person will appreciate that the bottom surface 304 of talar component 300 may have a variety of different shapes so long as the shape the talar dome is adapted to approximately mate with bottom surface 304 of talar component 300.

Figure 12:
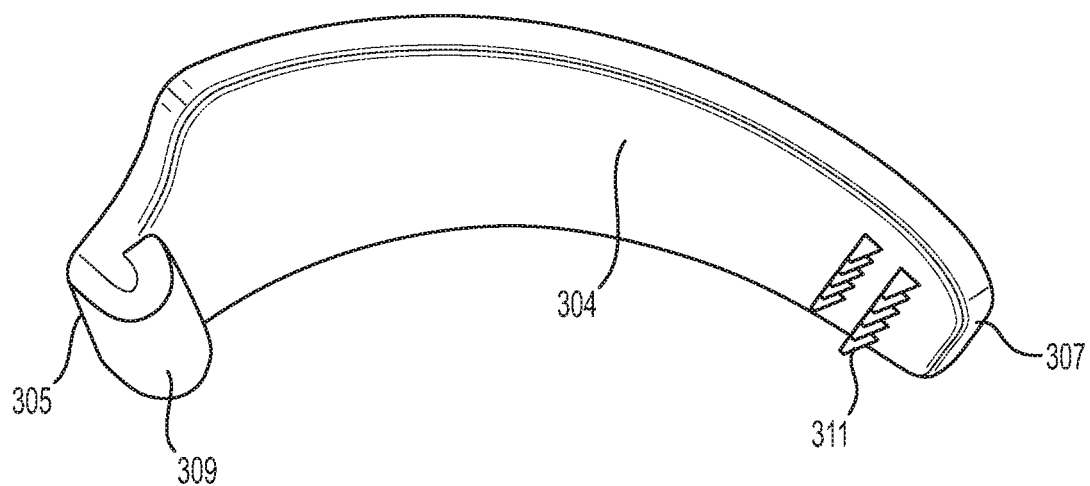
FIG. 12 shows a bottom perspective view of one embodiment of a talar component of the invention with spikes on the posterior end and a ridge on the anterior end.
Figure 13:
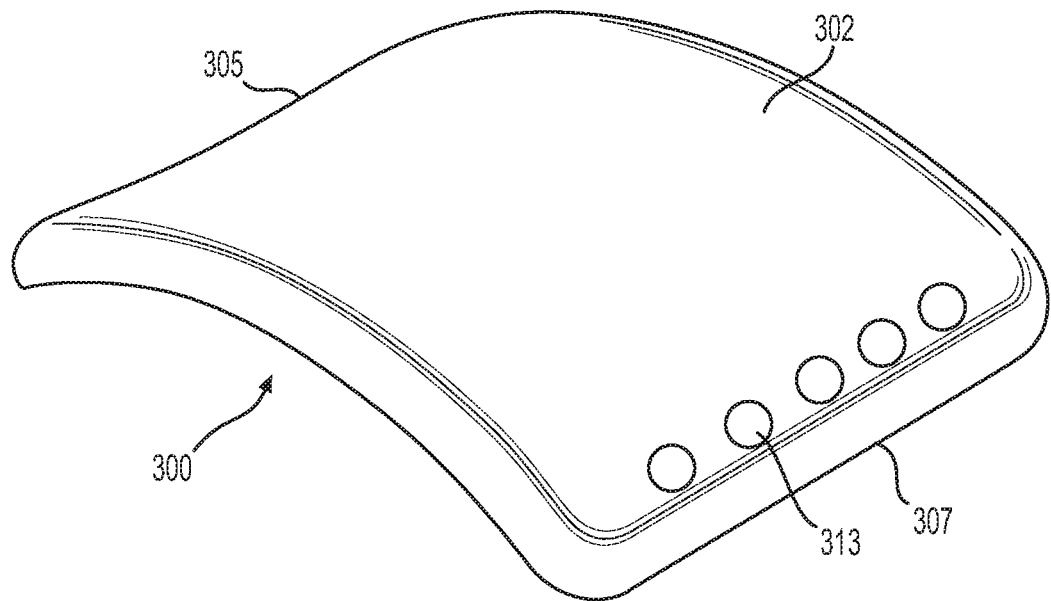
FIG. 13 shows a top perspective view of another embodiment of talar component of the invention with holes on the posterior end which may be used to affix the talar component to the talus using screws or other affixation devices.

In one embodiment, bottom surface 304 of talar component 300 has at least one protrusion or ridge 309 that extends downwardly from bottom surface 304. Such protrusions or ridges 309 are designed to fit with the shaped surface of the talar dome and provide an additional structure that can be used to secure talar component 300 to talus. The position of the protrusion(s) or ridge(s) 309 of the bottom surface 304 may vary. In one embodiment, a protrusion or ridge 309 may be located proximate to the anterior end 305 of the talar component 300 as shown in FIG. 12. In another embodiment, one protrusion or ridge 309 is located at the anterior end 305 of bottom surface 304, and spikes 311 are located on posterior end 307 of the bottom surface 304 as shown in FIG. 12. The spikes 311 are for penetrating into the talus thus affixing the talar component 300 to the talus. In yet another embodiment, holes 313 may be provide proximate to posterior end 307 of the talar component 300 as shown in FIG. 13. Holes 313 may be used to affix the talar component 300 to the talus using, for example, screws or other suitable attachment devices. In this embodiment, a ridge or protrusion 309 may also optionally be located on the anterior end 305.

Alternatively or additionally, the bottom surface 304 may be affixed to talar component using joining means other than the protrusions or ridges 309. Conventional joining means may include means such as adhesives, screws, friction fit, form fit and/or any combination thereof. Such means may include bone cement such as poly(methyl methacrylate), nails, plugs and any other suitable means known to skilled persons for affixing talar component 300 onto the talus.

Figure 8A:
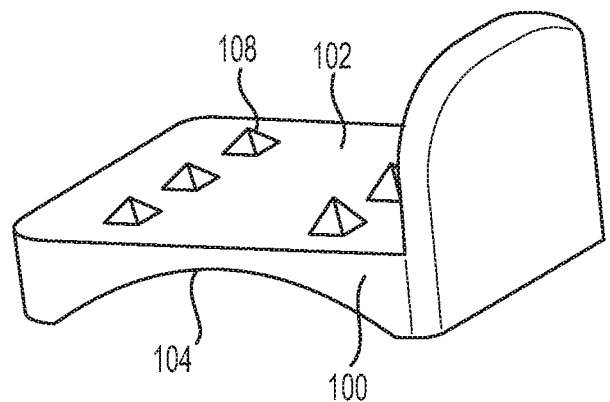
FIG. 8A depicts a tibial component of a prosthetic ankle according to one embodiment of the present invention.

Referring to FIG. 8A, the tibial component 100 of the prosthetic ankle may have a bottom surface 104 configured with a shape and curvature that substantially matches and complements aspects of the curvature of top surface 302 of the talar component 300. For example anterior end of the tibial component 100 may be aligned with and complement anterior end 305 of the talar component 300 with substantially matching curvatures, while posterior end of the tibial component 100 may be aligned with and complement posterior end 307 of talar component 300 with substantially matching curvatures. With this configuration, tibial component 100 can frictionally engage and move along top surface 302 of talar component 300. This configuration allows internal and external rotational motion of the ankle joint with the prosthetic ankle, as well as dorsiflexion and plantar flexion. The width of prosthetic ankle, from the medial side to the lateral side, may be in the range of from 15 mm to 35 mm, or from 18 mm to 33 mm, or from 20 mm to 30 mm.

Top surface 102 of tibial component 100 is adapted for affixation to the tibia. Thus top surface 102 may have a shape or configuration that matches and/or mates with the lower surface of the prepared/carved tibia. In one embodiment, as shown in FIG. 8A, top surface 102 may have one or more spikes 108 adapted for fixing the tibial component 100 onto the tibia. In another embodiment, referring to FIG. 14, the tibial component 100 may have one or more protrusions 109 extending in an anterior/posterior direction that are configured to match with the similarly shaped recesses that have been made in the prepared surface of the tibia. The spikes 108 and protrusions 109 serve to stabilize motion of tibial component 100 relative to the prepared distal tibial surface and provide greater surface area for bony ingrowth or cement fixation of tibial component 100 to the tibia. These protrusions or ridges 109 may be tapered, from more narrow on a medial side to wider on a lateral side, so as to create a more secure and stable fit.

Alternatively or additionally, top surface 102 of tibial component 100 may be affixed to the tibia using means other than protrusions 109 or spikes 108. Such means may include bone cement such as poly(methyl methacrylate), nails, plugs and any other means known to a skilled person to be useful for affixing the tibial component 100 onto the tibia. The tibial component 100 of the present invention is designed to be joined to the tibia during the implantation procedure using conventional joining means such as adhesives, screws, friction fit, form fit and/or any combination thereof.

Figure 8B:
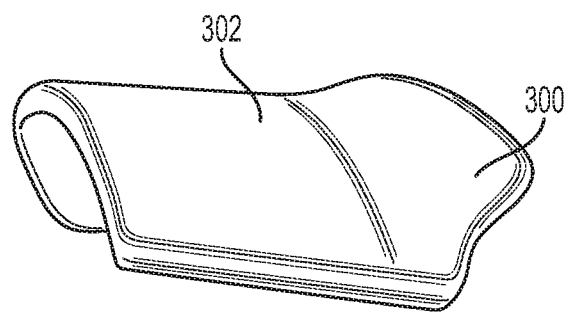
FIG. 8B depicts a talar component of a prosthetic ankle according to one embodiment of the present invention.

An example of talar component 300 is shown in FIG. 8B where top surface 302 of talar component 300 can be seen. Bottom surface 304 of talar component 300 and/or top surface 102 of tibial component 100 may be coated with a substance to enhance bony ingrowth or cement fixation.

Figure 14:
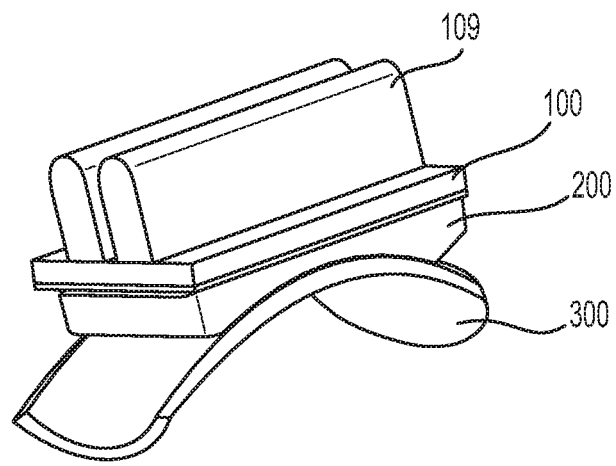
FIG. 14 shows a prosthetic ankle according to another embodiment of the present invention.
Figure 16A:
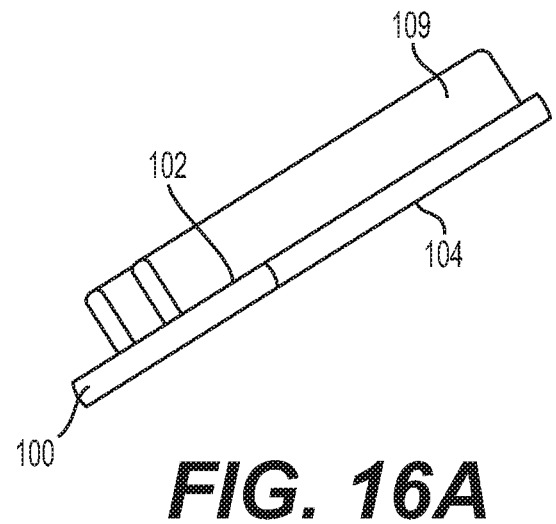
FIG. 16A shows a tibial component with a flat bottom surface according to one embodiment of the present invention.

In some alternative embodiments, the prosthetic ankle of the present invention includes a third component, namely, a bearing component 200 as shown in FIG. 14. In these alternative embodiments, the talar component 300 is the same as described above. The top surface 102 of the tibial component 100 is also the same as described above. However, the bottom surface 104 of the tibial component 100 may be flat as shown in FIG. 16A or have another suitable configuration for frictional engagement with top surface 202 of bearing component 200.

Figure 16B:
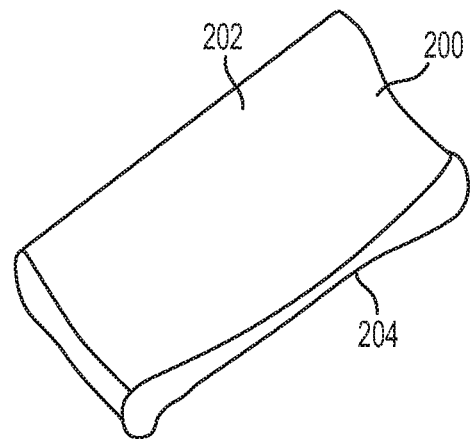
FIG. 16B shows a bearing component with a flat top surface adapted for use with the tibial component of FIG. 16A according to one embodiment of the present invention.

Bearing component 200 is designed for location between tibial component 100 and talar component 300 to provide bearing surfaces that allow relative motion between tibial component 100 and talar component 300. Top surface 202 of bearing component 200 may also be flat as shown in FIG. 16B, to match a flat bottom surface 104 of tibial component 100. Bottom surface 204 of bearing component 200 may be adapted to substantially match and/or complement the shape of top surface 302 of talar component 300. This configuration allows bearing component 200 to cooperatively engage both tibial component 100 and talar component 300 by frictional engagement. This enables relative movement between bearing component 200 and both tibial component 100 and talar component 300.

The thickness of bearing component 200 may be varied for adaptation of the prosthetic ankle for subjects having differences in the anatomy of their ankles. A suitable thickness of the bearing component 200 may be determined by examination of the ankle of the subject for which the prosthetic ankle is intended.

Selection of the thickness of bearing component 200 permits adjustment of the overall height of the prosthetic ankle. Thus, the present invention may provide a prosthetic ankle that is adaptable, depending on the thickness of the bearing component 200. This provides options for dealing with different clinical situations. Ultimately, the goal will be to use a prosthetic ankle that balances considerations of providing maximum range of movement, minimizing wear and enhancing the longevity of the implant.

In some embodiments, bearing component 200 may be semi-constrained. This may be achieved by using a tibial component 100 having a bottom surface 104 with one of a variety of forms of curvature that are designed to provide varying degrees of constraint on the motion relative to the underlying bearing component 200. A skilled person will appreciate that the curvature of bottom surface 104 of tibial component 100 and the curvature of top surface 202 of bearing component 200 may be altered in these embodiments to achieve the desired degree of constraint of motion.

Figure 15A:
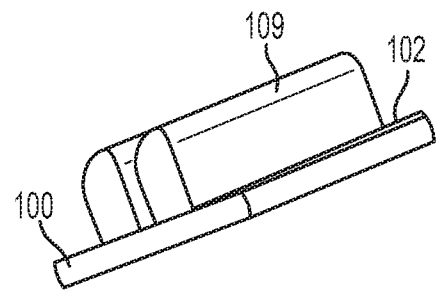
FIG. 15A shows an alternative embodiment of the tibial component of the present invention.
Figure 15B:
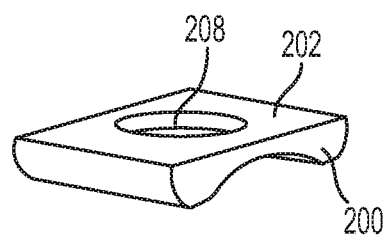
FIG. 15B shows an embodiment of a bearing component of a prosthetic ankle according to one embodiment of the present invention adapted for use with the tibial component of FIG. 15A.

To illustrate this, bottom surface 104 of tibial component 100 can be curved so that bottom surface 104 is configured for fitting with a curved portion of top surface 202 of bearing component 200. In one embodiment, shown in FIGS. 15A-15B, a plug 106 may be formed on bottom surface 102 of tibial component 100. Plug 106 is adapted to engage a corresponding recess 206 on top surface 202 of bearing component 200. Such a plug 106 can be located at any suitable location but in one embodiment is centrally located in bottom surface 104 of tibial component 100. The plug 106 can be of any suitable size, shape or configuration as desired and as can be appreciated by those of skill in the art in order to allow for a desired range of motion as the tibial component 100 and the bearing component 200 interact and articulate with one another.

In some other embodiments, top surface 202 of bearing component 200 may be bonded or mechanically attached to bottom surface 104 of tibial component 100. This may also provide a desired level of constraint on relative motion between the bearing component 200 and tibial component 100. More means of constraining or semi-constraining the mobility of bearing component 200 relative to tibial component 100 are disclosed in WO 2006/023824, which is hereby incorporated by reference in its entirety.

In these semi-constrained bearing embodiments, top surface 302 of talar component 300, bottom surface 204 of bearing component 200, and top surface 102 of tibial component 100 may be the same as in the unconstrained embodiments described above.

Tibial component 100 and talar component 300 may be made of the same or different materials and the materials may be selected from any appropriate material suitable for the surgical environment. High density, ultra-high molecular weight polyethylene is a suitable material for fabrication of these components. This material is widely used in other surgical devices and characterized by excellent wear resistance and a low coefficient of friction. Metallic alloys that are biocompatible are also suitable materials for the tibial and talar components 100, 300 of the present invention. Exemplary materials include titanium alloys and cobalt chrome alloys. Stainless steel or ceramics may also be used to fabricate the two components.

Bearing component 200 of the present invention is preferably made of a synthetic plastic material such as a high density, ultra-high molecular weight polyethylene that provides a low coefficient of friction and excellent wear resistance. The high density, ultra-high molecular weight polyethylene used in the present invention may have an extremely long chain with a molecular weight generally between 1 and 10 million Daltons, or between 2 and 6 million Daltons.

It will be understood by a skilled person that tibial component 100, bearing component 200, and talar component 300 will be made in left and right mirror-image embodiments and may be made in different sizes to accommodate subjects of different sizes. The size of the device does not constitute a limitation of the present invention. It is believed, for example, that a wide range of subjects can be accommodated by providing each of these components in three sizes. Bearing component 100 can also be made in several different thicknesses for the reasons given above.

EXAMPLE

Example 1

Morphological measurements were taken for a number of human talus bones. The measurements were taken from sagittal sections of the talus on both the medial and lateral sides. The average radius of curvature of the top surface of the talus was the overall radius of curvature in a particular sagittal section determined in accordance with the method of the present invention discussed above. The results are summarized in Table 1.

TABLE 1

| Morphology of Human Talus | | |
| --- | --- | --- |
| Morphological Measurements | Medial Radius (mm) | Lateral Radius (mm) |
| Average | 25.634 | 21.770 |
| Median | 25.129 | 21.420 |

From the data in Table 1, it can be seen that the natural curvature of the top surface of the talus as viewed in a sagittal plane on the medial side has a larger radius for both the average value and the median value, in comparison with the radius of the natural curvature on the lateral side. This is contrary to the current prevailing view presented by Inman's Joints that the curvature of the top surface of talus has larger radius on the lateral side than on the medial side.

The present invention provides a prosthetic ankle that reflects the natural morphology of human talus as determined using these measurements.

Example 2

A talar component 300 with its top surface 302 resembling a truncated cone as shown in FIG. 17 was designed. The truncated cone has an axis A-A that connects the centers of the medial circle 11 and lateral circle 12. Line B-B is a line perpendicular to the medial circle 11 and through its center. Line C-C is a line connecting the tips of the medial and lateral malleoli. In this design, the angle between lines A-A and B-B is 20.9° and the angle between lines A-A and C-C is 16°.

Comparative Example 1

Figure 18:
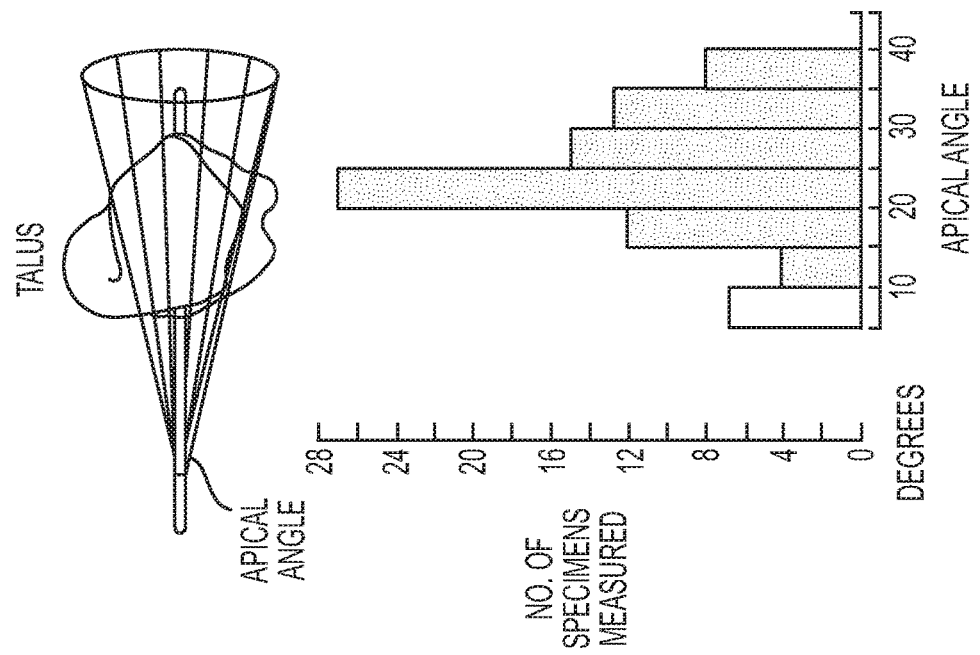
FIG. 18 depicts a cone used as a model for some prior art designs of ankle implants.

In a prior art design, the talar component of an ankle implant has a top surface resembling a truncated cone with its apex pointing to the medial side of the ankle (FIG. 18). Such a cone has a larger radius on the lateral side than on the medial side of the ankle implant. The apical angle of the cone is in a range of from about 0° to about 40°. This prior art design was based on an incorrect assumption that the ankle joint possesses a fixed axis of rotation, which has been refuted in several later studies. LUNDBERG, A., SVENSSON, O. K., NEMETH, G. & SELVIK, G. 1989. The axis of rotation of the ankle joint. $J$ Bone Joint Surg Br, 71, 94-9. SAMMARCO, J. 1977. Biomechanics of the ankle. I. Surface velocity and instant center of rotation in the sagittal plane. $Am\ J\ Sports\ Med$, 5, 231-4. SIEGLER, S., CHEN, J. & SCHNECK, C. D. 1988. The three-dimensional kinematics and flexibility characteristics of the human ankle and subtalar joints—Part I: Kinematics. $J\ Biomech\ Eng$, 110, 364-73. This incorrect assumption led to a prior art design of a talar component having its top surface resembling a truncated cone with a larger radius on the lateral side than on the medial side of the ankle implant. The prior art design thus placed the axis of the cone coinciding with the axis of rotation of the ankle as shown in FIGS. 19-21.

Figure 19:
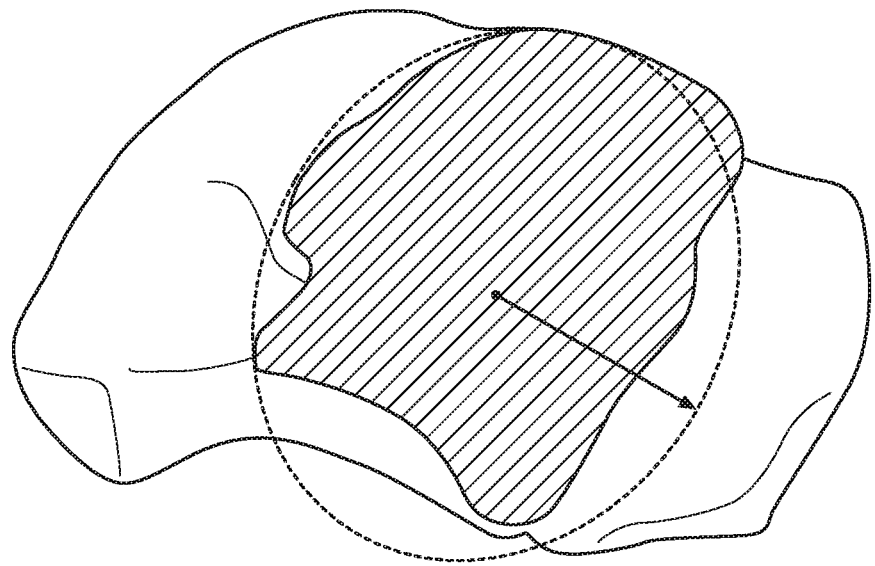
FIG. 19 depicts a cross-sectional view taken on the lateral side of the talus showing a circle centered about the assumed axis of rotation of the prior art comparative model of FIG. 18.
Figure 20:
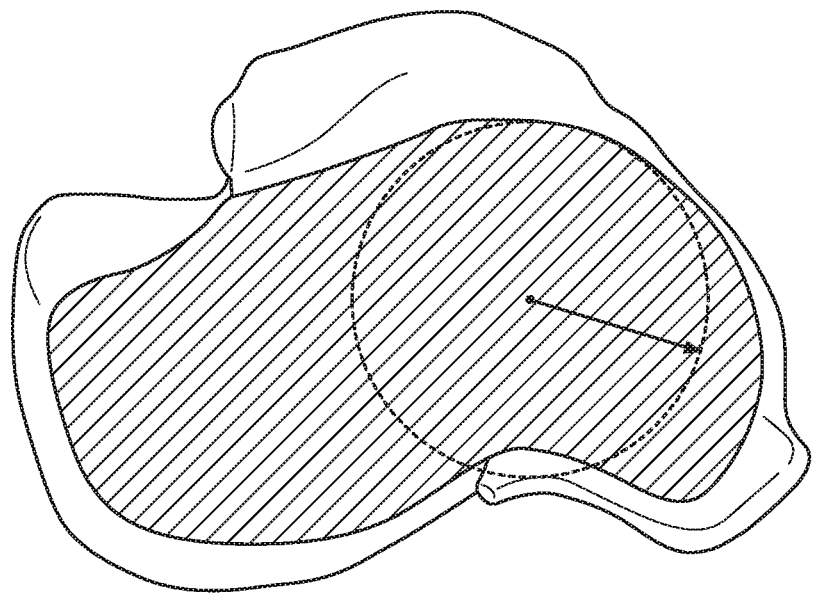
FIG. 20 depicts a cross-sectional view taken on the medial side of the talus showing a circle centered about the assumed axis of rotation of the prior art comparative model of FIG. 18.

More specifically, the truncated cone of FIG. 18 is arrived at by assuming an axis of rotation of the ankle as shown in FIGS. 19-20. Then, as shown in FIG. 19, a cross-section is taken on the lateral side of the talus and a circle centered about the assumed axis of rotation is drawn with the entire circle located within the cross-sectional surface. Similarly, as shown in FIG. 20, a cross-section is taken on the medial side of the talus and a circle centered about the assumed axis of rotation is drawn with the entire circle located within the cross-sectional surface. Then, a conical surface is generated by providing a surface tangent to each of the two circles, resulting in a cone with its apex on the medial side of the talus as shown in FIG. 21.

Since there is, in fact, no axis of rotation of the ankle as assumed for the purpose of this comparative model, this results in the generation of an incorrect conical representation of the talus. The correct conical representation of the talus is generated by the method of the present invention as described above which is not based on the incorrect assumption that the ankle joint rotates about a fixed axis of rotation.

Referring to Example 1 above, the morphological measurements taken from the human talus indicate that the average radius of curvature of the top surface of the talus is larger on the medial side of the ankle than on the lateral side. These measurements further substantiate that the prior art design is in conflict with the kinematic coupling behavior of the ankle joint.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

What is claimed is:

1. A prosthetic ankle comprising:
    a tibial component having a top surface for location adjacent to a tibia and a bottom surface; and
    a talar component having a bottom surface for location adjacent to a talus, and a top surface having:
    (a) a convex curvature relative to a location above the top surface, in an anterior to posterior direction as viewed in a sagittal plane cross-section, and
    (b) a concave curvature relative to a location above the top surface, in a medial to lateral direction as viewed in a frontal plane cross-section, and
    wherein an axis of a cone projected with the cone's apex pointing in a substantially lateral direction based on medial and lateral circles located in medial and lateral sagittal plane cross-sections of the talar component which approximate the average radius of curvature of the top surface of the talar component as viewed in medial and lateral sagittal plane cross-sections, has a total offset angle from the lateral direction in the range of 0° to 45°.

2. The prosthetic ankle of claim 1, wherein the total offset angle is in the range of 3° to 40°.

3. The prosthetic ankle of claim 1, wherein an average radius of curvature of at least a major portion of a medial side of the top surface of the talar component is substantially the same as an average radius of curvature of at least a major portion of a lateral side of the top surface of the talar component as viewed in sagittal plane cross-sections.

4. The prosthetic ankle of claim 1, wherein an average radius of curvature of at least a major portion of a medial side of the top surface of the talar component is larger than an average radius of curvature of at least a major portion of a lateral side of the top surface of the talar component as viewed in sagittal plane cross-sections.

5. The prosthetic ankle of claim 1, wherein the concave curvature of the top surface of the talar component decreases from an anterior end towards a posterior end of the talar component, as viewed in frontal plane cross-sections.

6. The prosthetic ankle of claim 1, wherein the cone has an apex angle in the range of from 2° to 30°.

7. The prosthetic ankle of claim 3, wherein the apex angle of the cone is in the range of from 3° to 20°.

8. The prosthetic ankle of claim 3, wherein an axis of the cone has a total axis offset angle in the range of from 5° to 35°.

9. The prosthetic ankle of claim 1, where a ratio of radii of medial and lateral circles located in medial and lateral sagittal plane cross-sections which approximate the average radius of curvature of the top surface of the talar component as viewed in medial and lateral sagittal plane cross-sections is from 1.5:1 to 1.01:1.

10. The prosthetic ankle of claim 7, where the ratio of the radii of medial and lateral circles is from 1.35:1 to 1.1:1.

11. The prosthetic ankle of claim 1, wherein the top surface of the talar component has a larger curvature on a medial side than on a lateral side, as viewed in a frontal-plane cross-section.

12. The prosthetic ankle of claim 1, wherein the tibial component has a bottom surface configured to substantially match the top surface of the talar component such that the talar and tibial components can move relative to one another and frictionally engage one another on the top surface of talar component and the top surface of the tibial component defines one or more structures selected from the group consisting of protrusions and ridges.

13. The prosthetic ankle of claim 1, further comprising a bearing component having a bottom surface configured to substantially mate with a top surface of the talar component and the bottom surface of the tibial component is configured for at least partially constraining the mobility of the bearing component relative to the tibial component.

14. A prosthetic ankle comprising:
    a tibial component having a top surface for location adjacent to a tibia and a bottom surface; and
    a talar component having a bottom surface for location adjacent to a talus, and a top surface having:
    (a) a convex curvature relative to a location above the top surface, in an anterior to posterior direction as viewed in a sagittal plane cross-section,
    (b) a concave curvature relative to a location above the top surface, in a medial to lateral direction as viewed in a frontal plane cross-section, and
    (c) an average radius of curvature of at least a major portion of a medial side of the top surface of the talar component is larger than an average radius of curvature of at least a major portion of a lateral side of the top surface of the talar component as viewed in sagittal plane cross-sections.

15. The prosthetic ankle of claim 14, wherein the concave curvature relative to a location above the top surface, in a medial to lateral direction as viewed in a frontal plane cross-section, extends from the medial side of the top surface of the talar component to the lateral side of the top surface of the talar component.

16. The prosthetic ankle of claim 14, wherein an axis of cone projected based on medial and lateral circles located in medial and lateral sagittal plane cross-sections of the talar component which approximate the average radius of curvature of the top surface of the talar component as viewed in medial and lateral sagittal plane cross-sections, has a total offset angle from the lateral direction in the range of 0° to 45°.

17. The prosthetic ankle of claim 16, wherein the total offset angle is in the range of 3° to 40°.

18. The prosthetic ankle of claim 14, wherein an average radius of curvature of at least a major portion of a medial side of the top surface of the talar component is larger than an average radius of curvature of at least a major portion of a lateral side of the top surface of the talar component as viewed in sagittal plane cross-sections.

19. The prosthetic ankle of claim 14, wherein the cone has an apex angle in the range of from 2° to 30° and the concave curvature of the top surface of the talar component decreases from an anterior end towards a posterior end of the talar component, as viewed in frontal plane cross-sections.

* * * * *